United States Patent [19]
Hartman et al.

[11] Patent Number: 5,948,668
[45] Date of Patent: *Sep. 7, 1999

[54] PRODUCTION OF ENZYMATICALLY ACTIVE RECOMBINANT CARBOXYPEPTIDASE B

[75] Inventors: Jacob Hartman, Holon; Netta Fulga, Tel Aviv; Simona Mendelovitch, Ramat Aviv; Marian Gorecki, Rehevot, all of Israel

[73] Assignee: Bio-Technology General Corp., Iselin, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/782,760

[22] Filed: Jan. 13, 1997

Related U.S. Application Data

[63] Continuation of application No. 08/378,233, Jan. 25, 1995, abandoned.

[51] Int. Cl.$^6$ .................................................. C12N 9/50
[52] U.S. Cl. ......................... 435/212; 530/415; 530/416
[58] Field of Search .......................... 435/212; 530/415, 530/416

[56] References Cited

U.S. PATENT DOCUMENTS

| | | | |
|---|---|---|---|
| 3,625,829 | 12/1971 | Schmidt-Kastner et al. | 435/226 |
| 4,511,503 | 4/1985 | Olson et al. | 530/422 |
| 4,650,762 | 3/1987 | Boross et al. | 435/180 |
| 5,206,161 | 4/1993 | Drayna et al. | 435/212 |
| 5,672,496 | 9/1997 | Fayerman et al. | 435/212 |

FOREIGN PATENT DOCUMENTS

| | | |
|---|---|---|
| A2 0588118 | 3/1994 | European Pat. Off. |
| 95/14096 | 5/1995 | WIPO |

OTHER PUBLICATIONS

Reeck et al., Biochemistry 11:3947–3955 (1972).

Márquez–Méndez, J. Biochem. Biophys. Meth. 24:51–61 (1992).

Marston, Biochem. J. 240:1–12 (1986).

Folk et al., J. Biol. Chem. 231:379–391 (1958).

Marinkovic et al., Biochem. Med. 22:1–10 (1979).

Padfield et al., Anal. Biochem. 171:294–299 (1988).

Eaton et al., J. Biol. Chem. 266:21833–21838 (1991).

Lipperheide et al., Biochim. Biophys. Acta 880:171–178 (1986).

Yamamoto et al., Isolation of a cDNA Encoding a Human Serum Marker for Acute Pancreatitis, The Journal of Biological Chemistry 267(4):2575–2581, Feb. 1992 (Exhibit E).

Clauser et al., Structural Characterization of the Rat Carboxypeptidase A1 and B Genes, The Journal of Biological Chemistry 263(33): 17837–17845, Nov. 1988 (Exhibit F).

Brodrick et al., Biochim. Biophys. Acta 452:468–481 (1976).

Bazzone et al., Biochemistry 18:4362–4366 (1979).

*Primary Examiner*—Charles L. Patterson, Jr.
*Assistant Examiner*—Enrique D. Longton
*Attorney, Agent, or Firm*—John P. White; Cooper & Dunham LLP

[57] ABSTRACT

The subject invention provides a method of producing enzymatically active CPB which comprises treating a recombinant cell containing DNA encoding ProCPB, so that the DNA directs expression of the ProCPB, recovering from the cell the ProCPB so expressed, treating the recovered ProCPB under conditions permitting folding of the ProCPB, subjecting the folded ProCPB to enzymatic cleavage to produce enzymatically active CPB and purifying the enzymatically active CPB.

9 Claims, 6 Drawing Sheets

FIGURE 1A
(SEQ. I.D. NOS. 1-7)

ProCPB 5'-end primer

```
       Nde I
5' GCG CAT ATG CAT GCT TCC GAG GAG CAC TTT GAT GGC 3'
                A1                                A10
               His Ala Ser Glu Glu His Phe Asp Gly Asn Arg Val Tyr Arg Val Ser
               CAT GCT TCC GAG GAG CAC TTT GAT GGC AAC CGG GTG TAC CGT GTC AGT
                           A20                                   A30
               Val His Gly Glu Asp Phe His Val Asn Leu Ile Gln Glu Leu Ala Asn Thr
               GTA CAT GGT GAA GAT TTC CAT GTC AAC TTA ATT CAG GAG CTA GCC AAC ACC
```

Activation Peptide

```
Lys Glu Ile Asp Phe Trp Lys Pro Asp Ser Ala Thr Gln Val Lys Pro
AAA GAG ATT GAT TTC TGG AAA CCA GAT TCT GCT ACA CAA GTG AAG CCT
           A40                                   A50
Leu Thr Thr Val Asp Phe His Val Lys Ala Glu Asp Val Ala Asp Val
CTC ACT ACA GTT GAC TTT CAT GTT AAA GCA GAA GAT GTT GCT GAT GTG
                                       A60                   A80
Glu Asn Phe Leu Glu Glu Asn Glu Val His Tyr Glu Val Leu Ile Ser
GAG AAC TTT CTG GAG GAG AAT GAA GTT CAC TAT GAG GTA CTG ATA AGC
                                           A70              A95
Asn Val Arg Asn Ala Leu Glu Ser Gln Phe Asp Ser His Thr Arg
AAC GTG AGA AAT GCT CTG GAA TCC CAG TTT GAT AGC CAC ACC CGT
```

FIGURE 1B
(SEQ. I.D. NOS. 1-7)

Mature CPB 5'-end primer

5' GC GCC ATG GCA AGT GGA CAC AGC TAC ACC AAG TAC AAC 3'

Mature CPB

```
 4                         10                                          20
Ala Ser Gly His Ser Tyr Thr Lys Tyr Asn Asn Trp Glu Thr Ile Glu Ala
GCA AGT GGA CAC AGC TAC ACC AAG TAC AAC AAC TGG GAA ACG ATT GAG GCG

30
    Trp Ile Gln Gln Val Ala Thr Asp Asn Pro Asp Leu Val Thr Gln Ser
    TGG ATT CAA CAA GTT GCC ACT GAT AAT CCA GAC CTT GTC ACT CAG AGC
                40                                  50
    Val Ile Gly Thr Thr Phe Glu Gly Arg Asn Met Tyr Val Leu Lys Ile
    GTC ATT GGA ACC ACA TTT GAA GGA CGT AAC ATG TAT GTC CTC AAG ATT
                                    60
    Gly Lys Thr Arg Pro Asn Lys Pro Ala Ile Phe Ile Asp Cys Gly Phe
    GGT AAA ACT AGA CCG AAT AAG CCT GCC ATC TTC ATC GAT TGT GGT TTC
         70                                         80
    His Ala Arg Glu Trp Ile Ser Pro Ala Phe Cys Gln Trp Phe Val Arg
    CAT GCA AGA GAG TGG ATT TCT CCT GCA TTC TGT CAG TGG TTT GTG AGA
                            90                                  100
    Glu Ala Val Arg Thr Tyr Asn Gln Glu Ile His Met Lys Gln Leu Leu
    GAG GCT GTC CGT ACC TAT AAT CAA GAG ATC CAC ATG AAA CAG CTT CTA
                                        110
    Asp Glu Leu Asp Phe Tyr Val Leu Pro Val Val Asn Ile Asp Gly Tyr
    GAT GAA CTG GAT TTC TAT GTT CTG CCT GTG GTC AAC ATT GAT GGC TAT
                120                                     130
    Val Tyr Thr Trp Thr Lys Asp Arg Met Trp Arg Lys Thr Arg Ser Thr
    GTC TAC ACC TGG ACT AAG GAC AGA ATG TGG AGA AAA ACC CGC TCT ACT
                                140
    Met Ala Gly Ser Ser Cys Leu Gly Val Asp Pro Asn Arg Asn Phe Asn
    ATG GCT GGA AGT TCC TGC TTG GGT GTA GAC CCC AAC AGG AAT TTT AAT
        150                                         160
    Ala Gly Trp Cys Glu Val Gly Ala Ser Arg Ser Pro Cys Ser Glu Thr
    GCT GGC TGG TGT GAA GTG GGA GCT TCT CGG AGT CCC TGC TCT GAA ACT
                            170                                 180
    Tyr Cys Gly Pro Ala Pro Glu Ser Glu Lys Glu Thr Lys Ala Leu Ala
    TAC TGT GGA CCA GCC CCA GAG TCT GAA AAA GAG ACA AAG GCC CTG GCA
```

FIGURE 1C
(SEQ. I.D. NOS. 1-7)

```
                                                  190
Asp Phe Ile Arg Asn Asn Leu*Ser Thr Ile Lys Ala Tyr Leu Thr Ile
GAT TTC ATC CGC AAC AAC CTC TCC ACC ATC AAG GCC TAC CTG ACC ATC
                        200                                  210
His Ser Tyr Ser Gln Met Met Leu Tyr Pro Tyr Ser Tyr Asp Tyr Lys
CAC TCA TAC TCA CAG ATG ATG CTC TAC CCT TAC TCC TAT GAC TAC AAA

Leu Pro Glu Asn Tyr Glu Glu Leu Asn Ala Leu Val Lys Gly Ala Ala
CTG CCT GAG AAC TAT GAG GAA TTG AAT GCC CTG GTG AAA GGT GCG GCA
                220                             240
Lys Glu Leu Ala Thr Leu His Gly Thr Lys Tyr Tyr Tyr Gly Pro Gly
AAG GAG CTT GCC ACT CTG CAT GGC ACC AAG TAC TAT ACA GGC CCA GGA
                    250
Ala Thr Ile Tyr Pro Ala Ala Gly Gly Ser Asp Asp Trp Ser Tyr
GCT ACA ATC TAT CCT GCT GCT GGG TCT GAC GAC TGG TCT TAT
260                                 270
Asp Gln Gly Ile Lys Tyr Ser Phe Thr Phe Glu Leu Arg Asp Thr Gly
GAT CAG GGA ATC AAA TAT TCC TTT ACC TTT GAA CTC CGG GAT ACA GGC
                                                            290
Phe Phe Gly Phe Leu Leu Pro Glu Ser Gln Ile Arg Gln Thr Cys Glu
TTC TTT GGC TTT CTC CTT CCT GAG TCT CAG ATC CGC CAG ACC TGT GAG
                        280                 300
Glu Thr Met Leu Ala Val Lys Tyr Ile Ala Asn Tyr Val Arg Glu His
GAG ACA ATG CTT GCA GTC AAG TAC ATT GCC AAT TAT GTC CGA GAA CAT

Leu Tyr *** ***
CTA TAT TAG TGA
GAT ATA ATC ACT CCT AGG CGC 5'
                         Bam HI
                                        3' TTA ATA CAG GCT CTT GTA

CPB 3'-end primer
```

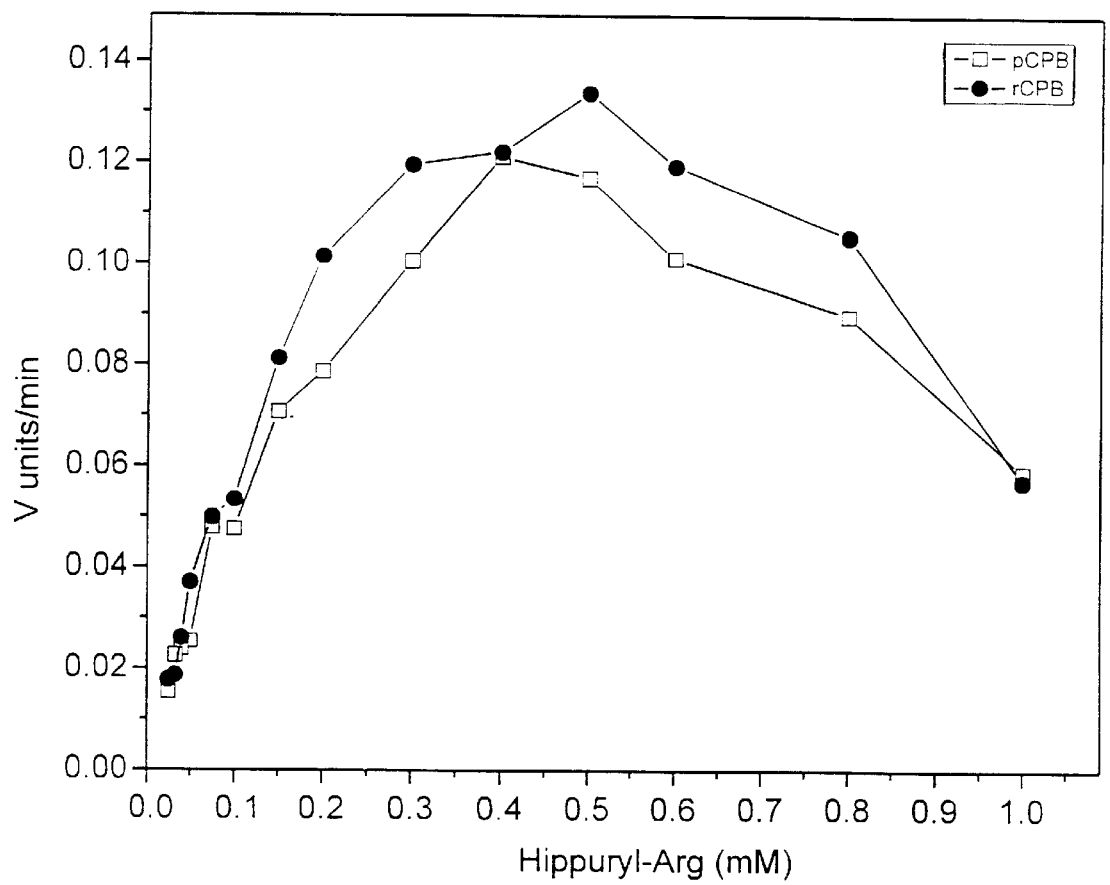

PRODUCTION OF ENZYMATICALLY ACTIVE RECOMBINANT CARBOXYPEPTIDASE B

This application is a continuation of U.S. Ser. No. 08/378,233, filed Jan. 25, 1995, now abandoned, the contents of which are hereby incorporated by reference.

BACKGROUND OF THE INVENTION

Throughout this specification, various publications are referenced by Arabic numerals within parentheses. Full citations for these references may be found at the end of the specification immediately preceding the claims. The disclosures of these publications in their entireties are hereby incorporated by reference into this specification in order to more fully describe the state of the art to which this invention pertains.

Naturally occurring carboxypeptidase B [Peptidyl-L-lysine (-L-arginine) hydrolase EC 3.4.17.2] is a zinc-containing pancreatic exopeptidase which specifically removes C-terminal Arg, Lys or Orn from peptides (1,2).

Naturally occurring rat carboxypeptidase B is produced from a precursor protein, preprocarboxypeptidase B, containing a 108 amino acid long N-terminal fragment which includes the signal sequence (13 amino acids) and an activation peptide (95 amino acids). Preprocarboxypeptidase B is enzymatically inactive.

During transport of preprocarboxypeptidase B to the endoplasmatic reticulum, the signal peptide is cleaved off; the resulting enzymatically inactive procarboxypeptidase B precursor is secreted from the cell. The enzymatically active carboxypeptidase B is then formed by cleavage of the activation peptide by trypsin (7).

Mature rat carboxypeptidase B contains 307 amino acids (5) and has an apparent molecular weight of 35 kD. It contains seven cysteine residues, six of which are paired into S—S bonds.

Carboxypeptidase B is widely used for commercial and research purposes, such as in the production of insulin and other biologically active polypeptides, and in protein sequence analysis.

Commercially available carboxypeptidase B purified from porcine pancreas is very expensive and is not totally free of other proteases.

The partial amino acid sequence of porcine precursor procarboxypeptidase B and the complete amino acid sequence of bovine carboxypeptidase B have been published (3, 4 respectively). In addition, the complete nucleotide sequence of the rat gene and the human cDNA have been published (5, 6 respectively).

Yamamoto et al. (6) have reported the recombinant expression of enzymatically inactive human procarboxypeptidase B lacking the first 11 amino acids of the activation peptide. They also report the recombinant expression of an enzymatically inactive β-galactosidase-procarboxypeptidase B fusion protein wherein the procarboxypeptidase is lacking the first 11 amino acids of the activation peptide.

European Publication No. 588118 A2 discloses a bone-related carboxypeptidase-like protein named OSF-5. It is speculated that OSF-5 acts as an adhesion molecule or a growth factor and that it can be used as an agent for treating bone metabolic diseases. However, no actual function or activity for OSF-5 has been disclosed and no production of either naturally-occurring or recombinant biologically active protein has been demonstrated.

The subject invention discloses the production of recombinant, highly purified, enzymatically active and non-expensive carboxypeptidase B. Production of enzymatically active carboxypeptidase B has not been previously reported and the disclosure here is novel.

SUMMARY OF THE INVENTION

The subject invention provides a method of producing enzymatically active carboxypeptidase B which comprises treating a recombinant cell containing DNA encoding pro-carboxypeptidase B, so that the DNA directs expression of the procarboxypeptidase B, recovering from the cell the procarboxypeptidase B so expressed, treating the recovered procarboxypeptidase B under conditions permitting folding of the procarboxypeptidase B, subjecting the folded procarboxypeptidase B to enzymatic cleavage to produce enzymatically active carboxypeptidase and purifying the enzymatically active carboxypeptidase B.

The subject invention further provides enzymatically active carboxypeptidase B.

BRIEF DESCRIPTION OF THE FIGURES

The restriction maps of the plasmids shown in FIGS. 2 and 3 do not identify all restriction sites present on the plasmids. However, those restriction sites necessary for a complete understanding of the invention are shown.

FIG. 1: Amino Acid and Corresponding cDNA Nucleotide Sequence of Pancreatic Rat Procarboxypeptidase B (SEQ ID NO:2)

The cDNA nucleotide sequence and corresponding amino acid sequence of pancreatic rat procarboxypeptidase B including the mature carboxypeptidase B nucleotide sequence (SEQ ID NO:5) and the activation peptide nucleotide sequence (SEQ ID NO:3) are shown. The DNA sequence differs from the DNA sequence published by Clauser et al. (5) by 4 nucleotides, two of which result in a change of amino acid: $Lys^{14} \rightarrow Asn$ and $Arg^{142} \rightarrow Asp$.

The DNA nucleotide sequence of three primers (SEQ ID NO:1, SEQ ID NO:7, SEQ ID NO:8) used during cloning (Example 1) are also shown (in large type): procarboxypeptidase B 5'-end primer, mature carboxypeptidase B 5'-end primer and carboxypeptidase B 3'-end primer.

The numeration of the amino acids was done according to the homology to carboxypeptidase A from bovine pancreas (10, 14), where the first amino acid (Ala) of mature rat carboxypeptidase B is numbered 4. The asterisk (*) indicates the additional amino acid (Leu) that rat carboxypeptidase B has in comparison to carboxypeptidase A.

Figure 2:
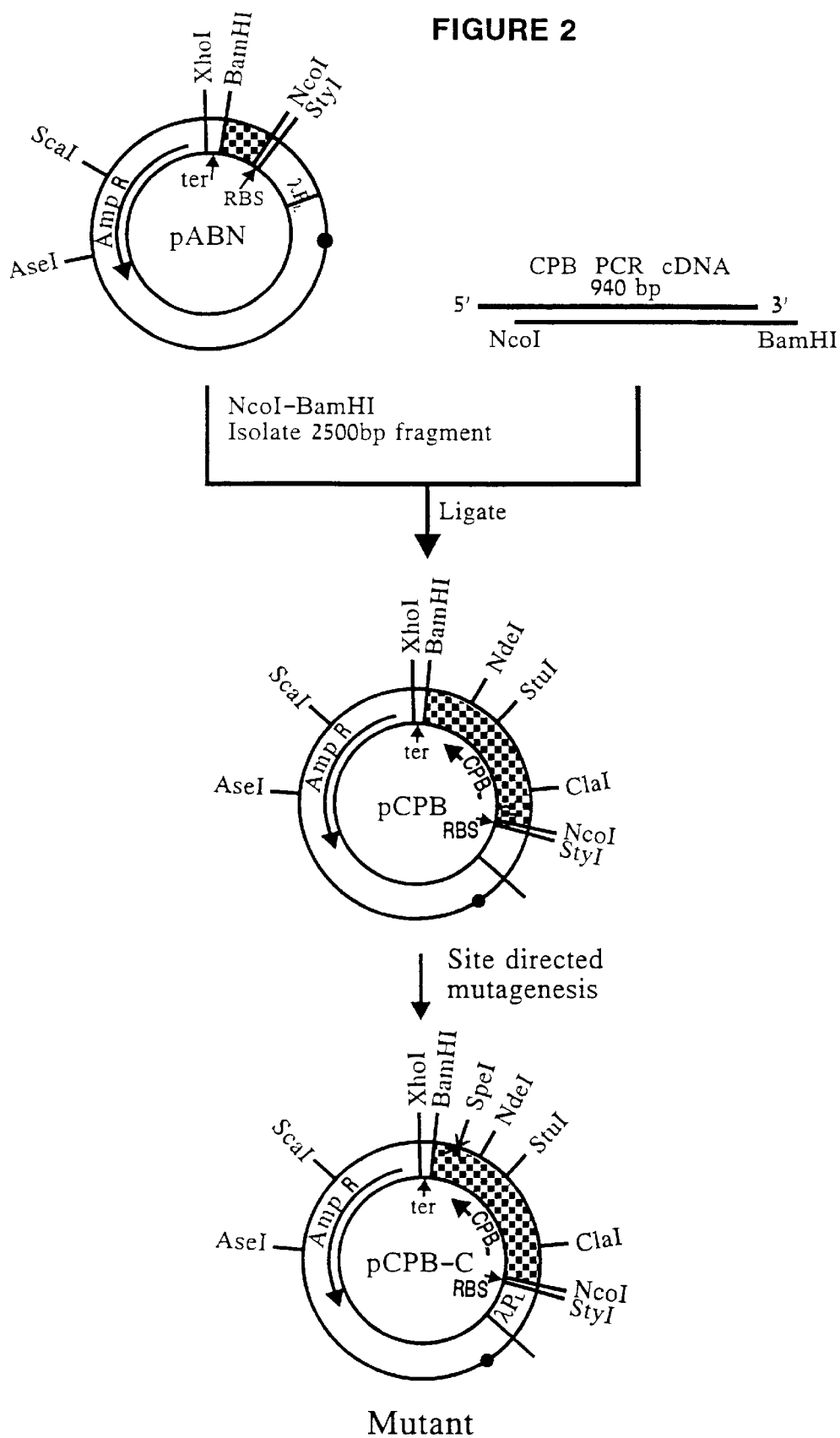

FIG. 2: Construction of Plasmid pCPB and Plasmid pCPB-C

Plasmid pABN was digested with BamHI and NcoI. The 2500 bp fragment was isolated and ligated to the BamHI-NcoI 940 bp carboxypeptidase B cDNA fragment (obtained as described in Example 1). The newly obtained plasmid was designated pCPB and was used to transform *E. coli* 4300.

Plasmid pCPB was digested with BamHI and NdeI in order to isolate the large fragment. Plasmid pCPB was also digested with AseI and ScaI in order to isolate the large fragment.

A heteroduplex was formed by mixing the two large fragments with a 5' terminal phosphorylated oligonucleotide prepared for site-specific mutagenesis (Example 1) and with polymerase-ligase buffer (5× buffer: 32.5 mM Tris-HCl pH 7.5, 40 mM MgCl$_2$, 5 mM 2-Mercaptoethanol, 0.5 M NaCl) (9). The mixture was boiled in order to denature the DNA strands and was gradually cooled in order to renature the DNA. The reaction products were used to transform *E. coli* 1645 by electroporation. Transformants were screened by growth on LB agar containing ampicillin and by in situ colony differential hybridization with the 5'-terminal phosphorylated oligonucleotide prepared for mutagenesis.

Plasmid DNA was extracted from positive colonies and, after restriction enzyme analysis and DNA nucleotide sequencing, a clone containing the mutant SpeI site was elected. The newly obtained plasmid was designated pCPB-C, which encodes carboxypeptidase B with a mutation at amino acid 290 from cysteine to serine. Plasmid pCPB-C was used to transform *E. coli* 4300.

Figure 3:
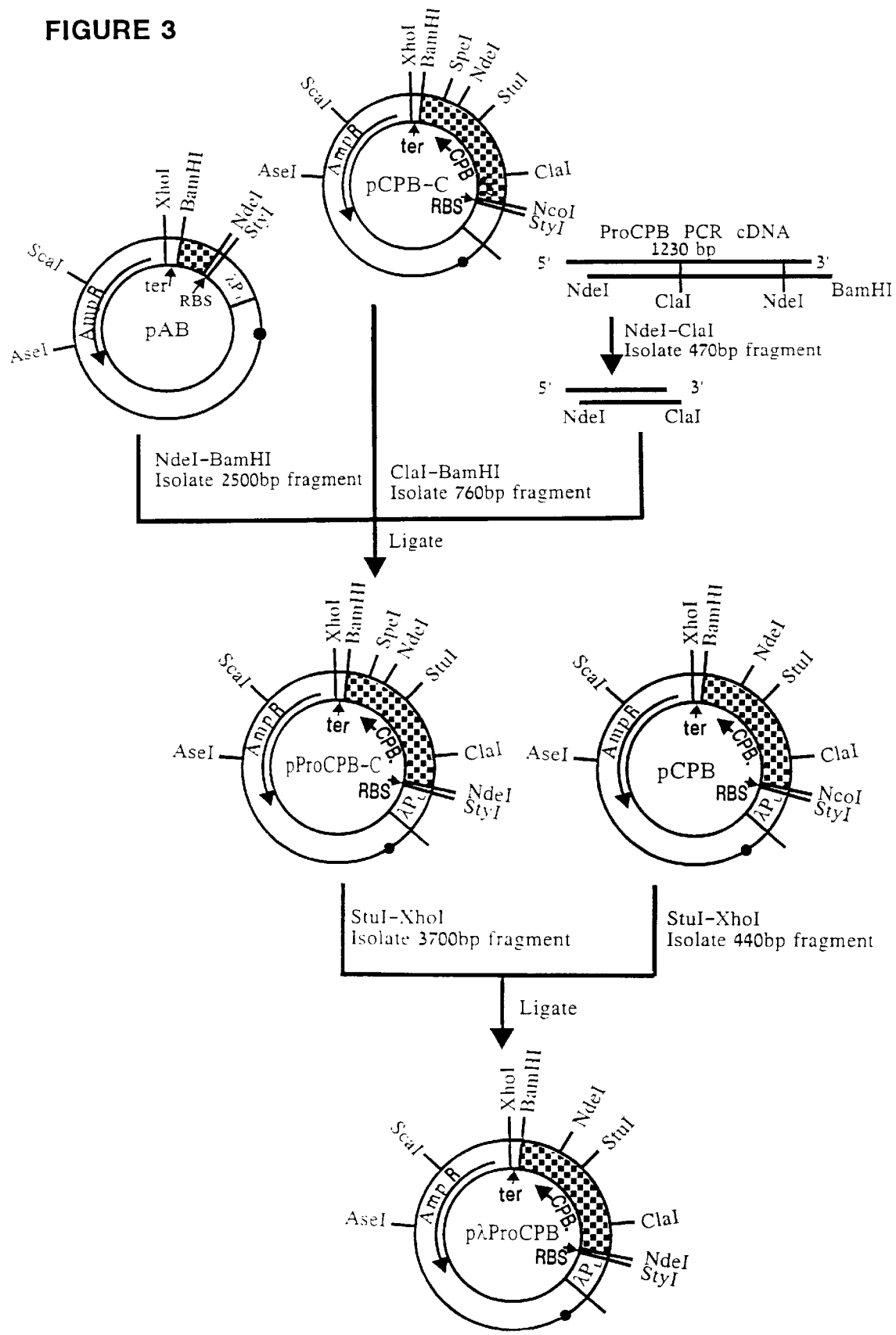

FIG. 3: Construction of Plasmid pProCPB-C and Plasmid pλProCPB

Procarboxypeptidase B cDNA, obtained as described in Example 1, was cleaved with NdeI and ClaI in order to isolate the 470 bp fragment which encodes the activation peptide and part of carboxypeptidase B.

Plasmid pCPB-C was cleaved with BamHI and ClaI in order to isolate the 760 bp fragment which encodes the remainder of carboxypeptidase B including the Cys$^{290}$→Ser mutation.

Plasmid pAB was cleaved with NdeI and BamHI in order to isolate the 2500 bp fragment which encodes all the elements necessary for expression in bacteria (see Example 1).

The above three fragments were ligated and the newly obtained plasmid was designated pProCPB-C.

Plasmids pProCPB-C and pCPB were cleaved with StuI and XhoI. A 3700 bp fragment, encoding all elements necessary for expression in bacteria (Example 1), the whole activation peptide and part of carboxypeptidase B, was isolated from plasmid ProCPB-C.

A 440 bp fragment, encoding the remainder of carboxypeptidase B, was isolated from plasmid pCPB.

The two fragments were ligated and the newly formed plasmid was designated pλProCPB.

FIG. 4: Comparison of Activity of Recombinant Carboxypeptidase B and Naturally Occurring Carboxypeptidase B The activity of commercial porcine carboxypeptidase B (Sigma) and of recombinant carboxypeptidase B made as described in Example 5 were determined according to the method of Folk (11) using Hippuryl-L-Arg substrate. $V_0$ of the catalytic reaction was measured using substrate concentrations between 0.025–0.1 mM.

DETAILED DESCRIPTION OF THE INVENTION

Plasmid pλProCPB was deposited in *E. coli* pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. 69673 on Aug. 4, 1994.

As used herein, "CPB" means a polypeptide whether made by recombinant DNA methods or otherwise, which has the same or substantially the same amino acid sequence as any naturally occurring mammalian carboxypeptidase B. Thus, the term CPB includes polypeptides which differ by one or more amino acids, preferably no more than about 10 amino acids, from naturally occurring carboxypeptidase Bs.

As used herein, "ProCPB" means a polypeptide whether made by recombinant DNA methods or otherwise, which has the same or substantially the same amino acid sequence as any naturally occurring mammalian procarboxypeptidase B. Thus, the term ProCPB includes polypeptides which differ by one or more amino acids, preferably no more than about 10 amino acids, from naturally occurring procarboxypeptidase Bs.

Persons skilled in the art can readily determine which amino acids residues may be added, deleted, or substituted (including with which amino acids such substitutions may be made) using established well known procedures, including, for example, conventional methods for the design and manufacture of DNA sequences coding for bacterial expression of polypeptides, the modification of cDNA and genomic sequences by site-directed mutagenesis techniques, the construction of recombinant proteins and expression vectors, the bacterial expression of the polypeptides, and the measurement of the biochemical activity of the polypeptides using conventional biochemical assays.

As used herein, an "enzymatically active" CPB means a CPB which possesses the biological activity of naturally occurring mammalian carboxypeptidase B. For the purpose of this definition the biological activity of a naturally occurring carboxypeptidase B is the ability to specifically remove a C-terminal arginine, lysine or ornithine from a peptide.

Substantially the same amino acid sequence is herein defined as encompassing substitutions and/or deletions and/or additions of amino acids in the amino acid sequence and may encompass up to ten (10) residues in accordance with the homologous or equivalent groups described by e.g. Lehninger, Biochemistry, 2nd ed. Worth Pub., N.Y. (1975), Chapter 4; Creighton, Protein Structure, a Practical Approach, IRL Press at Oxford Univ. Press, Oxford, England (1989); and Dayhoff, Atlas of Protein Sequence and Structure Vol. 5, The National Biomedical Research Foundation, Maryland (1972), Chapter 9. Such substitutions are known to those skilled in the art.

In a preferred embodiment, the DNA encoding ProCPB or CPB may be obtained from human, rat, bovine, or porcine origin. The DNA may be obtained by reverse transcription, polymerase chain reaction (PCR), synthetic or semi-synthetic means or by more than one of these methods or by other methods known in the art.

The DNA encoding the ProCPB or CPB polypeptide may be mutated by methods known to those skilled in the art, e.g. Bauer et al. (1985), Gene 37: 73–81. The mutated sequence may be inserted into suitable expression vectors as described herein, which are introduced into cells which are then treated so that the mutated DNA directs expression of a polypeptide.

Those skilled in the art will understand that the plasmid deposited in connection with this application may be readily altered by known techniques (e.g. by site-directed mutagenesis or by insertion of linkers) to encode expression of a polypeptide. Such techniques are described for example in Sambrook, J., Fritsch, E. F. and Maniatis, T. (1989) Molecular Cloning: A Laboratory Manual, 2nd edition, Cold Spring Harbor Laboratory Press.

Examples of vectors that may be used to express the nucleic acid encoding the CPB or ProCPB are viruses such as bacterial viruses, e.g., bacteriophages (such as phage lambda), cosmids, plasmids and other vectors. cDNA encoding ProCPB or CPB is inserted into appropriate vectors by methods well known in the art. For example, using conventional restriction endonuclease enzyme sites, inserts and vector DNA can both be cleaved to create complementary ends which base pair with each other and are then ligated together with a DNA ligase. Alternatively, synthetic linkers harboring base sequences complementary to a restriction site in the vector DNA can be ligated to the insert DNA, which is then digested with the restriction enzyme which cuts at that site. Other means are also available.

Vectors of the subject invention comprising a sequence encoding ProCPB or CPB may be adapted for expression in a range of prokaryotic and eucaryotic host cells, e.g. bacteria, yeast, fungi, insect cells or other mammalian cells such as CHO, chicken embryo, fibroblast, kidney or other known cell lines.

These vectors additionally comprise the regulatory elements necessary for expression of the cloned gene in the host cell so located relative to the nucleic acid encoding the ProCPB or CPB as to effect expression thereof.

Regulatory elements required for expression include promoter and operator sequences and a ribosomal binding site. For example, a bacterial expression vector may include a promoter-operator sequence such as $\lambda P_L O_L$ or deo promoters. For initiation of translation, the $\lambda C_{II}$ or deo ribosomal binding sites may be used. Such vectors may be obtained commercially or assembled from the sequences described by methods well known in the art, for example co-assigned U.S. Pat. No. 4,831,120, issued May 16, 1989 and co-assigned U.S. Pat. No. 5,143,836, issued Sep. 1, 1992, which disclose methods concerning the $\lambda P_L$ promoter and co-assigned European Patent Application Publication No. 303,972 published Feb. 22, 1989, which discloses methods concerning the deo promoter. Additional appropriate elements such as repressors and enhancers may also be present. Those skilled in the art know how to use regulatory elements appropriate for various expression systems.

The expression plasmids of this invention comprise suitable regulatory elements that are positioned within the plasmid relative to the DNA encoding the ProCPB or CPB polypeptide so as to effect expression of the ProCPB or CPB polypeptide in a suitable host cell. Such regulatory elements are promoters and operators, e.g. deo $P_1P_2$ and $\lambda P_L$, and ribosomal binding sites, e.g. deo and $C_{II}$, as well as repressors and enhancers.

In preferred embodiments of the invention, the regulatory elements are positioned close to and upstream of the DNA encoding the ProCPB or CPB.

The plasmids of the invention also contain an ATG initiation codon. The DNA encoding ProCPB or CPB is in phase with the ATG initiation codon.

The plasmids of the invention also include a DNA sequence comprising an origin of replication from a bacterial plasmid capable of autonomous replication in the host cell. Suitable origins of replication may be obtained from numerous sources, such as from plasmid pBR322 (ATCC Accession No. 37017).

The plasmids of the subject invention also include a DNA sequence which contains a gene associated with a selectable or identifiable phenotypic trait which is manifested when the plasmid is present in the host cell such as a drug resistance gene, e.g. resistance to ampicillin, chloramphenicol or tetracycline.

Preferred bacterial host cells are *E. coli* cells. An example of a suitable *E. coli* cell is strain 4300, but other *E. coli* strains and other bacteria can also be used as hosts for the plasmids.

The bacteria used as hosts may be any strain including auxotrophic (such as A1645), prototrophic (such as A4255), and lytic strains; F$^+$ and F$^-$ strains; strains harboring the cI$^{857}$ repressor sequence of the $\lambda$ prophage (such as A1645 and A4255) and strains devoid of the deo repressors and/or the deo gene (see European Patent Application Publication No. 0303972, published Feb. 22, 1989). *E. coli* strain 4300 has been deposited under ATCC Accession No. 69363.

All the *E. coli* host strains described above can be "cured" of the plasmids they harbor by methods well known in the art, e.g. the ethidium bromide method described by R. P. Novick in Bacteriol. Review 33, 210 (1969).

The subject invention provides a method of producing enzymatically active CPB which comprises treating a recombinant cell containing DNA encoding ProCPB, so that the DNA directs expression of the ProCPB, recovering from the cell the ProCPB so expressed, treating the recovered ProCPB under conditions permitting folding of the ProCPB, subjecting the folded ProCPB to enzymatic cleavage to produce enzymatically active CPB and purifying the enzymatically active CPB.

In a preferred embodiment, the recovering of the ProCPB from the recombinant cell comprises disrupting the cell wall of the recombinant cell or fragments thereof to produce a lysate, isolating intracellular precipitate from the lysate by centrifugation and solubilizing the intracellular precipitate in a suitable buffer.

In another embodiment, the treating of the recovered ProCPB comprises incubation of the ProCPB at room temperature for a period of about 20–24 hours at a pH of about 9–9.5.

In yet another embodiment, the treating of the recovered ProCPB comprises incubation of the ProCPB at room temperature for a period of about 20–24 hours at a pH of about 9–9.5 in the presence of $ZnCl_2$, oxidized glutathione (GSSG) and reduced glutathione (GSH).

It is envisaged that the subjecting of the folded ProCPB to enzymatic cleavage comprises adjusting the pH to about 8.5 and cleaving the ProCPB with trypsin at 37° C. for about 60 minutes.

It is further envisaged that the purifying of the enzymatically active CPB comprises ion-exchange chromatography.

It will be appreciated by those skilled in the art that any ion-exchange chromatography method can be used. A weak anion exchange column such as DEAE-Sepharose is preferred. Weak anion exchange columns usually have as functional group a tertiary amine (diaminoethyl), but amino ethyl is also possible.

The matrix may be based on inorganic compounds, synthetic resins, polysaccharides or organic polymers; possible matrices are agarose, cellulose, trisacryl, dextran, glass beads, oxiran acrylic beads, acrylamide, agarose/polyacrylamide copolymer or hydrophilic vinyl polymer.

It is also envisaged that the purifying of the enzymatically active CPB comprises ion-exchange chromatography and hydrophobic chromatography.

It will be appreciated by those skilled in the art that any hydrophobic column may be used. Phenyl-Sepharose is preferred. The functional group may be phenyl, benzyl, octyl or butyl. The matrix may be any of those discussed above.

In another preferred embodiment, the purifying of the enzymatically active CPB comprises ion-exchange chromatography, hydrophobic chromatography and diafiltration.

In a specifically preferred embodiment the ProCPB is expressed by plasmid pλProCPB deposited under ATCC Accession No. 69673.

The subject invention further provides enzymatically active CPB, free of other substances of mammalian origin.

EXAMPLES

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems. Such methods are well known to those of ordinary skill in the art and are described in numerous publications, the disclosures of which are hereby incorporated by reference into this specification, including by way of example the following:

Sambrook, J., Fritsch, E. F. and Maniatis, T. (1989) *Molecular Cloning: A Laboratory Manual,* 2nd edition, Cold Spring Harbor Laboratory Press.

Example 1: Cloning of Rat Carboxypeptidase B cDNA by PCR

I. DNA Amplification

Total RNA was extracted from pancreas of Sprague-Dawley rats. From total RNA, 40 μg of poly $A^+$ mRNA was isolated (by oligo dT-Cellulose column). An aliquot (10 μg) of the poly $A^+$ mRNA so obtained was used as a template in a reverse transcription reaction in the presence of a synthetic carboxypeptidase B 3'-end primer (5) (FIG. 1).

Following synthesis of the single stranded complementary DNA (ss-cDNA), the mRNA was precipitated with ethanol. An aliquot of the ss-cDNA was then subjected to PCR amplification:

For the amplification of the DNA encoding CPB (940 bp), a synthetic primer corresponding to the 3'-terminus of carboxypeptidase B and a synthetic primer corresponding to the 5'-terminus of mature carboxypeptidase B were used (FIG. 1).

For the amplification of the DNA encoding ProCPB (1230 bp), a synthetic primer corresponding to the 3'-terminus of carboxypeptidase B and a synthetic primer corresponding to the 5'-terminus of procarboxypeptidase B were used (FIG. 1).

The PCR amplification conditions were as follows:

| | | |
|---|---|---|
| 1. | Primer 3'-terminus | 2 μg |
| 2. | Primer 5'-terminus | 2 μg |
| 3. | ss-cDNA | 5 μl |
| 4. | Buffer: | |
| | dNTP's | 0.2 mM |
| | Tris-HCl | 50 mM |
| | KCl | 20 mM |
| | $MgCl_2$ | 8 mM |
| 5. | Taq Polymerase I | 2.5 units |
| | Total volume: | 100 μl |
| 6. | Mineral oil (against evaporation) | 50 μl |
| 7. | 1 cycle × [1' at 92° C.; 2' at 40° C. and 4' at 72° C.] | |
| 8. | 35 cycles × [1' at 92° C.; 2' at 53° C. and 3' at 72° C.] | |
| 9. | 1 cycle × [1' at 92° C.; 2' at 53° C. and 15' at 72° C.] | |

The PCR amplification products were analyzed on a 1% agarose gel. Non-amplified controls and size markers were also included. Two distinct bands of about 940 bp and 1230 bp were observed. The 940 bp band represents the CPB nucleotide sequence and the 1230 bp band represents the ProCPB nucleotide sequence which includes the activation peptide nucleotide sequence.

Following PCR amplification, the DNA was purified from the reaction mixture by chloroform and phenol extractions and ammonium acetate and isopropanol precipitation.

II. Plasmid pCPB

Plasmid pCPB (FIG. 2) was constructed by digesting the CPB cDNA with BamHI and NcoI and following gel purification, subcloning the fragment into the 2500 bp BamHI and NcoI fragment of plasmid pABN, which encodes the following elements necessary for expression in bacteria:

(i) $\lambda P_L$ promoter enabling gene expression from *E. coli* cells by induction, i.e. by shifting the temperature from 30° C. to 42° C. which inactivates the temperature sensitive repressor $cI^{857}$;

(ii) deo ribosomal binding site (rbs);

(iii) trp transcription terminator (8);

(iv) ampicillin resistance gene from plasmid pBR322; and (v) pBR322 origin of replication.

III. Plasmid pCPB-C

The naturally occurring carboxypeptidase B amino acid sequence contains 7 cysteine residues, six of which are paired in S-S bonds and one of which ($Cys^{290}$) is a free cysteine residue (1). We believed that this free cysteine residue might form undesired inter- or intra-molecular S—S bonds during refolding of the recombinant CPB. $Cys^{290}$ is not present in the catalytic site nor in the substrate binding site of carboxypeptidase B and apparently is not needed for the enzymatic activity of the enzyme (1,2). It was therefore decided to produce a CPB wherein this cysteine is replaced by serine; this CPB is designated CPB-C.

A 5' end phosphorylated oligonucleotide containing 2 nucleotide substitutions was prepared:

```
         Thr Cys
      ......ACC TGT......       original sequence in
                                carboxypeptidase B Thr Ser                                (Seq. ID
5' ATC CGC CAG ACT AGT GAG GAG ACA ATG 3'  No. 8)
               SpeI                                   mutant
                                                      sequence
```

This oligonucleotide was used in order to substitute the nucleotide sequence encoding $Cys^{290}$ with a nucleotide sequence encoding serine in plasmid pCPB by site-specific mutagenesis as described in FIG. 2 (9). The newly obtained plasmid was designated pCPB-C.

IV. Plasmid pProCPB-C

A plasmid designated pProCPB-C harboring the ProCPB-C nucleotide sequence (containing the $Cys^{290}$→Ser mutation) was constructed (FIG. 3) and used to transform *E. coli* 4300.

V. Plasmid pλProCPB

A plasmid designated pλProCPB containing the ProCPB nucleotide sequence was constructed (FIG. 3) and used to transform *E. coli* 4300. This plasmid was deposited with the ATCC under ATCC Accession No. 69673 on Aug. 4, 1994.

Plasmid DNA was prepared from plasmids pCPB, pCPB-C, pλProCPB, pProCPB-C, and was subjected to restriction enzyme analysis and nucleotide sequencing to verify the presence of the correct sequences.

Example 2: Fermentation, Growth Conditions and Purification of ProCPB and CPB I Stock Cultures Stock culture of *E. coli* 4300 harboring plasmid pλProCPB was grown on LB medium supplemented with ampicillin (100 µg/ml).

II Inoculum

The inoculum was propagated in 100 ml LB medium supplemented with ampicillin (100 g/ml) at 30° C. until cell concentration reached an O.D.$_{660}$ of 2.0.

The production medium (LB medium+ampicillin (100 µg/ml)) was inoculated, incubated at 30° C., aerated, agitated and the pH was maintained at 7.2 with NH$_3$. Twenty grams of glucose were added to the culture during growth. Once cell concentration reached an O.D.$_{660}$ of 12, the temperature was increased to 42° C. to enable expression of ProCPB. After two hours, cell concentration reached an O.D.$_{660}$ of 22–29 and the bacteria were harvested.

III Purification

ProCPB expressed by plasmid pλProCPB accumulated in intracellular precipitate which was isolated by the following procedure: 40 gram (wet weight) of bacterial cake was suspended in 450 ml buffer containing 1 mM PMSF (Sigma), 50 mM Tris-HCl, pH 8, 10 mM EDTA and was treated with lysozyme (Sigma) to a final concentration of 50 µg/ml, at 37° C. for 2 hours.

The mixture was then sonicated and Triton X-100 (Merck) was added to a final concentration of 2% and stirred for 2 hours at room temperature. Crude intracellular precipitate was pelleted by centrifugation (14000 rpm, 30 min., 4° C.) and washed with water.

Intracellular precipitate comprising ProCPB was dissolved in buffer B containing 25 mM NaCl, 8 M urea, 10 mM DTT, 20 mM Bis-Tris pH 7. The solution was chromatographed on DEAE-Sepharose Fast Flow column equilibrated in buffer B, the protein was eluted with about 100 mM NaCl in buffer B and ProCPB was precipitated with (NH$_4$)$_2$SO$_4$ at 40% saturation at 0° C.

It was later discovered that enzymatically active CPB could be produced only via production of the precursor protein. However, initially, the polypeptides CPB and CPB-C were produced in a similar manner to the production of ProCPB described above; ProCPB-C was also produced similarly. The plasmids used were pCPB, pCPB-C and pProCPB-C respectively (as described in Example 1). Growth conditions of *E. coli* harboring these plasmids and purification of the polypeptides were essentially as described above for ProCPB apart from the buffer used to dissolve intracellular precipitate comprising recombinant CPB or CPB-C which contained 20 mM Ethanolamine pH 9, 10 mM DTT and 8 M urea.

Note that in each case, the polypeptides produced and purified as described above had no enzymatic activity. The folding of the polypeptides in an attempt to produce enzymatically active proteins is described in Example 3.

Example 3: Folding and Activation of ProCPB-C

The polypeptides CPB and CPB-C were produced as described in Example 2, but were found to have no enzymatic activity. Known folding methods (as described below) were used but no enzymatically active protein was obtained.

In order to solve the problem of the inability to obtain enzymatically active protein, an alternative procedure was developed involving expression and folding of the precursor protein followed by treatment to remove the activation peptide portion of the folded precursor protein. This resulted in the process as described below.

ProCPB-C, produced as described in Example 2, was dissolved at 10 mg/ml in 8 M urea, 5 mM HCl and diluted to 1 mg/ml in 100 mM glycine, 0.2 mM ZnCl$_2$ at pH 9, 10 and 11. These were the folding solutions.

Folding was carried out by incubating the above folding solutions for 17 hours at room temperature. The ProCPB-C so produced had no enzymatic activity at this stage (see Table I).

The pH of the solution containing the folded ProCPB-C was then adjusted to about 8.5 with HCl and was treated with trypsin (1:200 w/w) for 30 minutes at 37° C. to remove the activation peptide. To terminate the reaction, PMSF was added to a final concentration of 0.1 mM.

The enzymatic activity of folded CPB-C so obtained was tested (Table I) according to Folk (1970)(11): One unit of activity (u) is defined as the amount of enzyme that catalyzes the hydrolysis of 1 µmol of Hippuryl-L-Arg substrate per minute at 25° C., causing an increase in absorbance of 0.12 at 254 nm and 1 cm path length. The specific activity of commercial porcine carboxypeptidase B (Sigma) is 230 u/mg.

TABLE I

Specific activity of ProCPB-C (and of CPB-C derived therefrom) under various conditions

| Reaction | Specific Activity (µ/mg) |
| --- | --- |
| 1. Substrate only | 0.0 |
| 2. Folding at pH 9, trypsin treatment, no ProCPB-C present | 0.0 |
| 3. Folding at pH 9, trypsin treatment | 4.3 |
| 4. Folding at pH 9 only | 0.0 |
| 5. Folding at pH 10, trypsin treatment | 1.7 |
| 6. Folding at pH 11, trypsin treatment | 0.3 |
| 7. Commercial porcine CPB | 230 |

Table I indicates that enzymatically active CPB-C was obtained after folding of ProCPB-C and trypsin treatment of the folded ProCPB-C using the preliminary conditions described above.

Table I further indicates that the specific activity of CPB-C is higher when the pH in the folding mixture is 9 than when the pH in the folding mixture is 10 or 11.

Example 4: Improved Folding Conditions

The following experiments were performed so as to establish optimal folding and activation conditions. We assumed that the higher the specific activity of CPB-C obtained by trypsin cleavage of the folded ProCPB-C, then the more optimal were the folding conditions of ProCPB-C. The "substrate only" and the "commercial porcine carboxypeptidase" controls were carried out in addition to the experiments below.

Initially, the results (as described in Example 3) were improved when folding was performed using 0.05–0.1 mg/ml ProCPB-C at pH 9.5.

I. The Effect of Temperature on Folding of ProCPB-C

Folding of ProCPB-C was carried out by incubation of 0.05 mg/ml polypeptide in 100 mM glycine, pH 9.5 for 90 hours at temperatures between 10–37° C. Samples of folded ProCPB-C were treated with trypsin (1:200 w/w) and the specific activity of CPB-C so obtained was measured as described in Example 3. Highest specific activity of CPB-C was obtained when folding of ProCPB-C was carried out between 20° C.–30° C.

II. The Effect of Oxidized and Reduced Glutathione on Folding of ProCPB-C

Folding of ProCPB-C was carried out by incubation of 0.05 mg/ml polypeptide in 100 mM glycine buffer pH 9.5, 0.01 mM $ZnCl_2$ at 25° C. in the presence of oxidized and/or reduced glutathione (GSSG/GSH) or ascorbic acid (Table II). Subsequently, the incubated solutions were treated with trypsin (1:200 w/w) for 1 hour at 37° C. and the specific activity of CPB-C so obtained was measured (as described in Example 3) after 18 and 45 hours.

TABLE II

Specific activity of CPB-C as a function of the presence of oxidant/reductant in the folding solution

| Oxidant/reductant added to folding solution | Specific Activity (u/mg) | |
|---|---|---|
| | 18 Hours | 45 Hours |
| 0.1 mM GSSG | 2.18 | 16.39 |
| 0.1 mM GSSG, 1 mM GSH | 16.37 | 26.90 |
| 16.5 μM ascorbic acid* | 4.06 | 9.24 |
| Control (none of the above added) | 1.19 | 5.39 |

*Ascorbic acid was added at a concentration of 2.5 mol to one mol SH group.

Table II indicates that the combined addition of GSSG and GSH causes a dramatic increase in the specific activity of CPB-C and therefore presumably in the folding efficiency of ProCPB-C. GSSH alone also increased the folding efficiency of ProCPB-C and so did ascorbic acid, although to a lower extent.

In another series of experiments it was found that optimal folding of ProCPB-C is obtained by the addition of 0.1 mM GSSG and 0.5 mM GSH to the folding solution.

III. Activation of Folded ProCPB-C by Trypsin

It was established that the most active CPB-C was obtained by tryptic cleavage of ProCPB-C to remove the activation peptide when the incubated folding solution was treated with trypsin 1:50 w/w for 1 hour at 37° C.

IV. The Effect of the pH on the Folding of ProCPB-C

The effect of pH on the folding of ProCPB-C was determined in a series of reactions under previously optimized conditions.

Folding of ProCPB-C was carried out at 0.1 mg/ml in 100 mM glycine, 0.02 mM $ZnCl_2$, 0.5 mM reduced glutathione (GSH), 0.1 mM oxidized glutathione (GSSG) at 25° C., for 24 hours at various pH values (between 8.75–10.00). Samples of folded ProCPB-C were treated with trypsin (1:50 w/w; dissolved in 1 mM HCl, 10 mM $CaCl_2$) and the specific activity of CPB-C so obtained was measured as described in Example 3.

Highest specific activity of CPB-C was obtained when folding of ProCPB-C was carried out at pH 9.25.

V. The Effect of $ZnCl_2$ on the Folding of ProCPB-C

The effect of $ZnCl_2$ concentration in the folding solution on the folding of ProCPB-C was determined in a series of reactions under previously optimized conditions. At a $ZnCl_2$ concentration 2–20 fold higher than the estimated CPB-C concentration (mol/mol), the specific activity of CPB-C produced was highest. When folding was carried out without addition of $ZnCl_2$, and EDTA was added to the folding mixture to chelate any residual divalent ions, the specific activity of CPB-C decreased to zero.

VI. The Effect of the Protein Concentration on the Folding of ProCPB-C

Folding of ProCPB-C was carried out for 24 hours under optimal conditions (as determined above) at the indicated protein concentrations in Table III. After tryptic digestion the activity of CPB-C was measured as described in Example 3.

TABLE III

Specific activity of CPB-C as a function of the protein concentration in the folding solution

| Protein concentration (mg/ml) | Specific Activity (u/mg) |
|---|---|
| 0.05 | 35.1 |
| 0.10 | 31.8 |
| 0.20 | 20.3 |

Table III indicates that the specific activity of CPB-C produced was highest at a protein concentration of 0.05 mg/ml.

VII. Folding Time as a Function of the Specific Activity of CPB-C

The optimal folding time of ProCPB-C was determined in a series of reactions under previously optimized conditions.

Folding of ProCPB-C was carried out at 0.1 mg/ml in 100 mM glycine, pH 9.25, 0.1 mM GSSG, 0.5 mM GSH and 0.01 M $ZnCl_2$. Samples of folded ProCPB-C were treated with trypsin (1:50 w/w) and the specific activity of CPB-C so obtained was measured as described in Example 3 at various time points (between 0–40 hours) from the initiation of folding.

Highest activity of CPB-C was obtained when the folded ProCPB-C was cleaved with trypsin after 20 hours from the initiation of folding. Folding for more than 20 hours did not change the specific activity of CPB-C.

Example 5: Folding and Activation of the Different CPB Proteins

CPB, CPB-C, ProCPB and ProCPB-C produced and purified as described in Example 2 were each folded at 0.1 mg/ml in 100 mM glycine buffer, pH 9.25, 0.01 mM $ZnCl_2$, 0.5 mM GSH, 0.1 mM GSSG at room temperature for 24 hours, i.e. the folding conditions used were essentially the optimal conditions established in Example 4.

The pH of each solution containing the folded CPB, CPB-C, ProCPB or ProCPB-C was adjusted to 8.5 with HCl and the solutions containing ProCPB and ProCPB-C were treated with trypsin (1:50 w/w) for 1 hour at 37° C. to remove the activation peptide. To terminate the reaction, PMSF was added to a final concentration of 0.1 mM. Specific activity of CPB, CPB-C, ProCPB and ProCPB-C was measured as described in Example 3.

TABLE IV

Specific activity of CPB, CPB-C, ProCPB and
ProCPB-C after folding and activation at optimal
conditions

| Folding | Specific Activity (u/mg) |
|---|---|
| Controls[1] | |
| no trypsin treatment | 0.00 |
| no protein | 0.00 |
| Folding | |
| CPB | 0.00 |
| CPB-C | 0.08 |
| ProCPB | 42.90 |
| ProCPB-C | 20.90 |

[1]The control "no trypsin" was done for ProCPB-C only.

Table IV indicates that enzymatically active CPB can be produced only from cells expressing the precursor containing the activation peptide. Thus, the activation peptide is necessary for correct folding of CPB.

Table IV also indicates that CPB with optimal specific activity is produced from folding and activation of ProCPB (expressed by plasmid pλProCPB) which contains the free $Cys^{290}$ residue and not from folding and activation of ProCPB-C which contains the $Cys^{290} \rightarrow Ser$ mutation. Thus, $Cys^{290}$ is apparently needed for optimal folding and/or highest activity of CPB.

Example 6: Improved Folding of ProCPB

I. Folding of ProCPB from Crude Intracellular Precipitate

Optimal folding conditions for ProCPB were found to be essentially identical to the optimal folding conditions for ProCPB-C determined in Example 4.

A simplified method for folding and activation of ProCPB was carried out by using crude intracellular precipitate, omitting the need for the initial purification step as described in Example 2, part III.

It was found that crude intracellular precipitate containing ProCPB (produced as described in Example 2) could be dissolved at high protein concentrations (Table V) in 100 mM glycine, pH 9.5 and 8 M urea.

Folding was carried out under optimized conditions for 24 hours at room temperature. The pH was raised to the optimal pH of 9.5 (previously determined). The folded ProCPB was cleaved with trypsin (1:50 w/w) and the specific activity of CPB was measured as described in Example 3.

TABLE V

Specific activity of CPB as a function of
the protein concentration in the folding solution
comprising crude intracellular precipitate

| Protein Concentration (mg/ml) | Specific Activity (u/mg) |
|---|---|
| 0.1 | 10.5 |
| 0.2 | 10.9 |
| 0.5 | 11.9 |
| 1.0 | 12.1 |
| 2.0 | 11.4 |

Table V indicates that enzymatically active CPB may be obtained by folding of ProCPB from crude intracellular precipitate, followed by tryptic digestion. Moreover, the CPB is enzymatically active at a similar level at all protein concentrations measured. This is an unexpected result, since the specific activity of CPB, purified on DEAE-Sepharose before folding (Example 2), decreased when the protein concentration increased in the folding mixture. Apparently, the intracellular precipitate contains factors assisting folding of ProCPB.

II. Scaling Up of CPB by Folding of ProCPB from Crude Intracellular Precipitate (i) Production CPB was purified to near homogeneity from 42 liters *E. coli* 4300 harboring plasmid pλProCPB and expressing ProCPB.

The fermentation and growth conditions were essentially as described in Example 2.

The crude intracellular precipitate was washed in water and was dissolved at 20 mg/ml in 100 mM glycine, pH 9.5, 8 M urea and were diluted to 1 mg/ml with 100 mM glycine, pH 9.5. 0.1 mM $ZnCl_2$, 0.5 mM GSH and 0.1 mM GSSG were added and the resulting folding solution was incubated at 25° C. for 24 hours. The pH was then adjusted to 8.5 with HCl and the folded ProCPB was digested with trypsin (20 μg/ml) at 37° C. for 1 hour. Trypsin was inactivated with 0.1 mM PMSF.

(ii) Purification

The enzymatically active CPB was loaded onto DEAE-Sepharose Fast-Flow column (Pharmacia) equilibrated with 20 mM Tris-HCl, pH 8 at 20 mg per ml resin. CPB was eluted with 80 mM NaCl, 20 mM Tris-HCl, pH 8. Ammonium sulfate (0.8 M) was added to the DEAE elution pool which was further chromatographed on Phenyl-Sepharose Fast-Flow column (Pharmacia) equilibrated with 20 mM Tris-HCl pH 8, 0.8 M ammonium-sulfate. CPB was eluted with 0.4 M ammonium sulfate, concentrated, diafiltered against 100 mM NaCl, 20 mM Tris-HCl, pH 8 and stored at −20° C.

In the above purification process, 42 liters of *E. coli* 4300 harboring plasmid pλProCPB at $O.D._{660}$=36 were processed as described above and 1.25 gram of enzymatically active CPB with a specific activity of 637 u/mg was obtained. The overall process yield was about 60%.

The specific activity of commercial porcine carboxypeptidase B, measured under identical experimental conditions, was 298 u/mg.

Example 7: Characterization of Enzymatically Active CPB

CPB produced as discussed in Examples 5 and 6 has biochemical and enzymatic properties comparable to porcine carboxypeptidase B.

The extinction coefficient of recombinant CPB, calculated on the basis of its amino acid composition is $\epsilon^{1\%}_{280}=19.7$. The extinction coefficient of commercial porcine carboxypeptidase B is $\epsilon^{1\%}_{280}=21.4$ (1).

Recombinant CPB has a specific activity of 637 u/mg (Hippuryl-L-Arg substrate) and contains 1 mol of Zn per mol enzyme as determined by atomic absorption.

N-terminal amino acid sequence analysis revealed Ala-Ser-Gly-His-Ser, as expected from the amino acid sequence analysis of mature rat carboxypeptidase B (5).

The optimal pH for recombinant CPB activity was determined using 25 mM of the following buffers: NaOAc, pH 4–6; Bis-Tris, pH 6–7.5; Tris-HCl pH 7.5–9; and Glycine, pH 9–12. The CPB specific activity was measured as described in Example 3. The optimal enzymatic activity of CPB was obtained at pH 8. Incubation of CPB at 55° C. caused 50% loss of activity and complete inactivation occurred at 65° C.

Kinetic analysis of recombinant CPB was performed using Hippuryl-L-Arg substrate (FIG. 4). There was inhibition of CPB activity at substrate concentrations above 0.5 mM.

Additional studies revealed that recombinant CPB was inhibited by the catalysis product arginine, which is a competitive inhibitor of carboxypeptidase B. The corresponding Lineweaver-Burk curve showed a Km value of 0.38 mM.

Recombinant CPB was also inhibited by 1,10-phenanthroline, a strong divalent ion chelator, thus demonstrating the importance of Zn ions for enzymatic activity of CPB. In the presence of 1 mM 1,10 phenanthroline, 50% loss of activity of 1 mg/ml recombinant CPB is observed.

Example 8: Conversion of Proinsulin to Insulin by CPB

Mini-proinsulin, as described in EP 347781 B1, may be converted to insulin by treatment with trypsin and recombinant CPB as produced in Examples 5 and 6.

Trypsin cleaves specifically between the arginine residue and the A chain. CPB subsequently specifically hydrolyses the arginine residue from the C-terminus of the B chain.

Commercial human insulin (Boehringer-Mannheim) may be used as a standard as well as the mini-proinsulin cleaved by trypsin and commercial porcine carboxypeptidase B, and the mini-proinsulin cleaved by trypsin alone.

REFERENCES

1. Barrett and McDonald (1985), Mammalian proteases, a Glossary and Bibliography, Vol. 2, Academic Press, Orlando, Fla.
2. Coll et al. (1991), The Embo J. 10: 1–9.
3. Burgos et al. (1991), Biochemistry 30: 4082–4089.
4. Titani et al. (1975), P.N.A.S. 72: 1666–1670.
5. Clauser et al. (1988), J. Biol. Chem. 263 (33): 17837–17845.
6. Yamamoto et al. (1992), J. Biol. Chem. 267: 2575–2581.
7. Aviles et al. (1985), Biochem. and Bioph. Res. Comm. 130: 97–103.
8. Yanofsky et al. (1981), Nucleic Acid Res. 9: 6647–6668
9. Morinaga et al. (1984), Bio-Technology July: 636–639.
10. Bradshaw et al. (1969), P.N.A.S. 63: 1389–1394.
11. Folk (1970), Methods in Enzymology 19: 504–508.
12. Bradford (1976), Anal. Chem. 72: 248–254.
13. Lowry (1951), J. Biol. Chem. 193: 265–275.
14. Gardell et al. (1988), J. Biol. Chem. 263(33) :17828–17836.
15. Sherman et al. (1983), P.N.A.S. 80: 5465–5469.

---

What is claimed is:

1. A method of producing an enzymatically active mammalian pancreatic CPB which has the amino acid sequence and enzymatic activity of a naturally-occurring mammalian pancreatic CPB which comprises the following steps in the order recited:

(a) treating a recombinant bacterial cell containing DNA encoding ProCPB, so that the DNA directs expression of ProCPB;

(b) solubilizing the ProCPB so expressed at pH 7–9.5;

(c) incubating the solubilized ProCPB at a pH of about 9–9.5 permitting folding of the ProCPB;

(d) subjecting the folded ProCPB to enzymatic cleavage to produce enzymatically active CPB; and (e) purifying the enzymatically active CPB.

2. A method according to claim 1 wherein the solubilizing of step (b) comprises:

(a) disrupting the cell wall of the recombinant cell to produce a lysate;

(b) isolating intracellular precipitate from the lysate by centrifugation; and (c) solubilizing the intracellular precipitate in a suitable buffer.

3. A method according to claim 1 wherein the incubating of step (c) is carried out at room temperature for a period of about 20–24 hours.

4. A method according to claim 1 wherein the incubating of step (c) is carried out at room temperature for a period of about 20–24 hours in the presence of $ZnCl_2$, oxidized glutathione and reduced glutathione.

5. A method according to claim 1 wherein the subjecting of step (d) comprises:

(i) adjusting the pH to about 8.5; and
   (ii) cleaving the ProCPB with trypsin at 37° C. for about 60 minutes.

6. A method according to claim 1 wherein the purifying of step (e) comprises ion-exchange chromatography.

7. A method according to claim 1 wherein the purifying of step (e) comprises ion-exchange chromatography and hydrophobic chromatography.

8. A method according to claim 1 wherein the purifying of step (e) comprises ion-exchange chromatography, hydrophobic chromatography and diafiltration.

9. A method according to claim 1 wherein the ProCPB is expressed by plasmid pλProCPB deposited under ATCC Accession No. 69673.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

GCGCATATGC ATGCTTCCGA GGAGCACTTT GATGGC      36

(2) INFORMATION FOR SEQ ID NO:2:

(i) SEQUENCE CHARACTERISTICS:
      (A) LENGTH: 285 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..285

(xi) SEQUENCE DESCRIPTION: SEQ ID NO:2:

| | | | | | | | | | | | | | | | | |
|---|---|---|---|---|---|---|---|---|---|---|---|---|---|---|---|---|
| CAT | GCT | TCC | GAG | GAG | CAC | TTT | GAT | GGC | AAC | CGG | GTG | TAC | CGT | GTC | AGT | 48 |
| His | Ala | Ser | Glu | Glu | His | Phe | Asp | Gly | Asn | Arg | Val | Tyr | Arg | Val | Ser | |
| 1 | | | | 5 | | | | | 10 | | | | | 15 | | |
| GTA | CAT | GGT | GAA | GAT | CAC | GTC | AAC | TTA | ATT | CAG | GAG | CTA | GCC | AAC | ACC | 96 |
| Val | His | Gly | Glu | Asp | His | Val | Asn | Leu | Ile | Gln | Glu | Leu | Ala | Asn | Thr | |
| | | | 20 | | | | | 25 | | | | | 30 | | | |
| AAA | GAG | ATT | GAT | TTC | TGG | AAA | CCA | GAT | TCT | GCT | ACA | CAA | GTG | AAG | CCT | 144 |
| Lys | Glu | Ile | Asp | Phe | Trp | Lys | Pro | Asp | Ser | Ala | Thr | Gln | Val | Lys | Pro | |
| | | | 35 | | | | | 40 | | | | | 45 | | | |
| CTC | ACT | ACA | GTT | GAC | TTT | CAT | GTT | AAA | GCA | GAA | GAT | GTT | GCT | GAT | GTG | 192 |
| Leu | Thr | Thr | Val | Asp | Phe | His | Val | Lys | Ala | Glu | Asp | Val | Ala | Asp | Val | |
| | | 50 | | | | | 55 | | | | | 60 | | | | |
| GAG | AAC | TTT | CTG | GAG | GAG | AAT | GAA | GTT | CAC | TAT | GAG | GTA | CTG | ATA | AGC | 240 |
| Glu | Asn | Phe | Leu | Glu | Glu | Asn | Glu | Val | His | Tyr | Glu | Val | Leu | Ile | Ser | |
| 65 | | | | | 70 | | | | | 75 | | | | | 80 | |
| AAC | GTG | AGA | AAT | GCT | CTG | GAA | TCC | CAG | TTT | GAT | AGC | CAC | ACC | CGT | | 285 |
| Asn | Val | Arg | Asn | Ala | Leu | Glu | Ser | Gln | Phe | Asp | Ser | His | Thr | Arg | | |
| | | | | 85 | | | | | 90 | | | | | 95 | | |

(2) INFORMATION FOR SEQ ID NO:3:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:3:

```
His Ala Ser Glu Glu His Phe Asp Gly Asn Arg Val Tyr Arg Val Ser
 1               5                  10                  15

Val His Gly Glu Asp His Val Asn Leu Ile Gln Glu Leu Ala Asn Thr
            20                  25                  30

Lys Glu Ile Asp Phe Trp Lys Pro Asp Ser Ala Thr Gln Val Lys Pro
            35                  40                  45

Leu Thr Thr Val Asp Phe His Val Lys Ala Glu Asp Val Ala Asp Val
        50                  55                  60

Glu Asn Phe Leu Glu Glu Asn Glu Val His Tyr Glu Val Leu Ile Ser
65                  70                  75                  80

Asn Val Arg Asn Ala Leu Glu Ser Gln Phe Asp Ser His Thr Arg
                85                  90                  95
```

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

GCGCCATGGC AAGTGGACAC AGCTACACCA AGTACAAC                    38

(2) INFORMATION FOR SEQ ID NO:5:

(i) SEQUENCE CHARACTERISTICS:

(A) LENGTH: 927 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 1..927

(xi) SEQUENCE DESCRIPTION: SEQ ID NO:5:

```
GCA AGT GGA CAC AGC TAC ACC AAG TAC AAC AAC TGG GAA ACG ATT GAG         48
Ala Ser Gly His Ser Tyr Thr Lys Tyr Asn Asn Trp Glu Thr Ile Glu
                100                 105                 110

GCG TGG ATT CAA CAA GTT GCC ACT GAT AAT CCA GAC CTT GTC ACT CAG         96
Ala Trp Ile Gln Gln Val Ala Thr Asp Asn Pro Asp Leu Val Thr Gln
        115                 120                 125

AGC GTC ATT GGA ACC ACA TTT GAA GGA CGT AAC ATG TAT GTC CTC AAG        144
Ser Val Ile Gly Thr Thr Phe Glu Gly Arg Asn Met Tyr Val Leu Lys
130                 135                 140

ATT GGT AAA ACT AGA CCG AAT AAG CCT GCC ATC TTC ATC GAT TGT GGT        192
Ile Gly Lys Thr Arg Pro Asn Lys Pro Ala Ile Phe Ile Asp Cys Gly
        145                 150                 155

TTC CAT GCA AGA GAG TGG ATT TCT CCT GCA TTC TGT CAG TGG TTT GTG        240
Phe His Ala Arg Glu Trp Ile Ser Pro Ala Phe Cys Gln Trp Phe Val
160                 165                 170                 175

AGA GAG GCT GTC CGT ACC TAT AAT CAA GAG ATC CAC ATG AAA CAG CTT        288
Arg Glu Ala Val Arg Thr Tyr Asn Gln Glu Ile His Met Lys Gln Leu
                180                 185                 190

CTA GAT GAA CTG GAT TTC TAT GTT CTG CCT GTG GTC AAC ATT GAT GGC        336
Leu Asp Glu Leu Asp Phe Tyr Val Leu Pro Val Val Asn Ile Asp Gly
        195                 200                 205

TAT GTC TAC ACC TGG ACT AAG GAC AGA ATG TGG AGA AAA ACC CGC TCT        384
Tyr Val Tyr Thr Trp Thr Lys Asp Arg Met Trp Arg Lys Thr Arg Ser
            210                 215                 220

ACT ATG GCT GGA AGT TCC TGC TTG GGT GTA GAC CCC AAC AGG AAT TTT        432
Thr Met Ala Gly Ser Ser Cys Leu Gly Val Asp Pro Asn Arg Asn Phe
225                 230                 235

AAT GCT GGC TGG TGT GAA GTG GGA GCT TCT CGG AGT CCC TGC TCT GAA        480
Asn Ala Gly Trp Cys Glu Val Gly Ala Ser Arg Ser Pro Cys Ser Glu
240                 245                 250                 255

ACT TAC TGT GGA CCA GCC CCA GAG TCT GAA AAA GAG ACA AAG GCC CTG        528
Thr Tyr Cys Gly Pro Ala Pro Glu Ser Glu Lys Glu Thr Lys Ala Leu
                260                 265                 270

GCA GAT TTC ATC CGC AAC AAC CTC TCC ACC ATC AAG GCC TAC CTG ACC        576
Ala Asp Phe Ile Arg Asn Asn Leu Ser Thr Ile Lys Ala Tyr Leu Thr
        275                 280                 285

ATC CAC TCA TAC TCA CAG ATG ATG CTC TAC CCT TAC TCC TAT GAC TAC        624
Ile His Ser Tyr Ser Gln Met Met Leu Tyr Pro Tyr Ser Tyr Asp Tyr
            290                 295                 300

AAA CTG CCT GAG AAC TAT GAG GAA TTG AAT GCC CTG GTG AAA GGT GCG        672
Lys Leu Pro Glu Asn Tyr Glu Glu Leu Asn Ala Leu Val Lys Gly Ala
305                 310                 315

GCA AAG GAG CTT GCC ACT CTG CAT GGC ACC AAG TAC ACA TAT GGC CCA        720
Ala Lys Glu Leu Ala Thr Leu His Gly Thr Lys Tyr Thr Tyr Gly Pro
320                 325                 330                 335

GGA GCT ACA ACA ATC TAT CCT GCT GCT GGG GGA TCT GAC GAC TGG TCT        768
Gly Ala Thr Thr Ile Tyr Pro Ala Ala Gly Gly Ser Asp Asp Trp Ser
                340                 345                 350
```

```
TAT GAT CAG GGA ATC AAA TAT TCC TTT ACC TTT GAA CTC CGG GAT ACA      816
Tyr Asp Gln Gly Ile Lys Tyr Ser Phe Thr Phe Glu Leu Arg Asp Thr
            355                 360                 365

GGC TTC TTT GGC TTT CTC CTT CCT GAG TCT CAG ATC CGC CAG ACC TGT      864
Gly Phe Phe Gly Phe Leu Leu Pro Glu Ser Gln Ile Arg Gln Thr Cys
            370                 375                 380

GAG GAG ACA ATG CTT GCA GTC AAG TAC ATT GCC AAT TAT GTC CGA GAA      912
Glu Glu Thr Met Leu Ala Val Lys Tyr Ile Ala Asn Tyr Val Arg Glu
385                 390                 395

CAT CTA TAT TAG TGA                                                  927
His Leu Tyr *   *
400
```

(2) INFORMATION FOR SEQ ID NO:6:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Ser Gly His Ser Tyr Thr Lys Tyr Asn Asn Trp Glu Thr Ile Glu
 1               5                  10                  15

Ala Trp Ile Gln Gln Val Ala Thr Asp Asn Pro Asp Leu Val Thr Gln
                20                  25                  30

Ser Val Ile Gly Thr Thr Phe Glu Gly Arg Asn Met Tyr Val Leu Lys
            35                  40                  45

Ile Gly Lys Thr Arg Pro Asn Lys Pro Ala Ile Phe Ile Asp Cys Gly
    50                  55                  60

Phe His Ala Arg Glu Trp Ile Ser Pro Ala Phe Cys Gln Trp Phe Val
65                  70                  75                  80

Arg Glu Ala Val Arg Thr Tyr Asn Gln Glu Ile His Met Lys Gln Leu
                85                  90                  95

Leu Asp Glu Leu Asp Phe Tyr Val Leu Pro Val Val Asn Ile Asp Gly
            100                 105                 110

Tyr Val Tyr Thr Trp Thr Lys Asp Arg Met Trp Arg Lys Thr Arg Ser
        115                 120                 125

Thr Met Ala Gly Ser Ser Cys Leu Gly Val Asp Pro Asn Arg Asn Phe
130                 135                 140

Asn Ala Gly Trp Cys Glu Val Gly Ala Ser Arg Ser Pro Cys Ser Glu
145                 150                 155                 160

Thr Tyr Cys Gly Pro Ala Pro Glu Ser Glu Lys Glu Thr Lys Ala Leu
                165                 170                 175

Ala Asp Phe Ile Arg Asn Asn Leu Ser Thr Ile Lys Ala Tyr Leu Thr
            180                 185                 190

Ile His Ser Tyr Ser Gln Met Met Leu Tyr Pro Tyr Ser Tyr Asp Tyr
        195                 200                 205

Lys Leu Pro Glu Asn Tyr Glu Glu Leu Asn Ala Leu Val Lys Gly Ala
    210                 215                 220

Ala Lys Glu Leu Ala Thr Leu His Gly Thr Lys Tyr Thr Tyr Gly Pro
225                 230                 235                 240

Gly Ala Thr Thr Ile Tyr Pro Ala Ala Gly Gly Ser Asp Asp Trp Ser
                245                 250                 255

Tyr Asp Gln Gly Ile Lys Tyr Ser Phe Thr Phe Glu Leu Arg Asp Thr
            260                 265                 270
```

```
Gly Phe Phe Gly Phe Leu Leu Pro Glu Ser Gln Ile Arg Gln Thr Cys
        275                 280                 285

Glu Glu Thr Met Leu Ala Val Lys Tyr Ile Ala Asn Tyr Val Arg Glu
        290                 295                 300

His Leu Tyr
305

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:7:

CGCGGATCCT CACTAATATA GATGTTCTCG GACATAATT                                      39

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:8:

ATCCGCCAGA CTAGTGAGGA GACAATG                                                   27
```